(12) United States Patent
Gwen

(10) Patent No.: US 6,748,958 B1
(45) Date of Patent: Jun. 15, 2004

(54) FLOSSER APPARATUS WITH FLOSS TIGHTENING MECHANISM

(76) Inventor: Patrick Gwen, 3443 Leeland, Houston, TX (US) 77003

( * ) Notice: Subject to any disclaimer, the term of this patent is extended or adjusted under 35 U.S.C. 154(b) by 22 days.

(21) Appl. No.: 10/172,054

(22) Filed: Jun. 17, 2002

(51) Int. Cl.$^7$ ............................................. A61C 15/00
(52) U.S. Cl. ..................................................... 132/327
(58) Field of Search ......................... 132/323, 324–327

(56) References Cited

U.S. PATENT DOCUMENTS

| | | | |
|---|---|---|---|
| 2,187,899 A | | 1/1940 | Henny |
| 2,648,341 A | | 8/1953 | Moll |
| 3,378,017 A | * | 4/1968 | Stiles ........................... 132/324 |
| 3,631,869 A | * | 1/1972 | Espinosa ..................... 132/323 |
| 3,783,883 A | * | 1/1974 | Alexander ................... 132/323 |
| D251,075 S | * | 2/1979 | Schiff .......................... D28/68 |
| 4,280,518 A | | 7/1981 | Gambaro |
| D276,088 S | | 10/1984 | Fong |
| 4,522,216 A | | 6/1985 | Bunker |
| 5,016,660 A | | 5/1991 | Boggs |
| 5,538,023 A | | 7/1996 | Oczkowshi |
| 5,692,531 A | | 12/1997 | Chodorow |
| 5,829,458 A | | 11/1998 | Chodorow |
| 6,065,479 A | * | 5/2000 | Chodorow .................. 132/323 |

FOREIGN PATENT DOCUMENTS

| | | |
|---|---|---|
| DE | 29 23 057 | 12/1982 |
| DE | 38 31 039 | 3/1990 |

* cited by examiner

*Primary Examiner*—Kevin Shaver
*Assistant Examiner*—Stephanie L Willatt
(74) *Attorney, Agent, or Firm*—Harrison & Egbert

(57) ABSTRACT

A flosser apparatus having a body with a first fork member and a second fork member, a flexible member interposed between the fork members, and a length of floss having one end affixed to the first fork member and an opposite end affixed to the second fork member. The flexible member is cooperative with the fork members such that the fork members move away from each other upon an application of a force onto the flexible member in a direction to the direction of the length of floss. The pivot point for the fork members is on an opposite of the flexible member from the length of floss.

12 Claims, 3 Drawing Sheets

FLOSSER APPARATUS WITH FLOSS TIGHTENING MECHANISM

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to appliances for using floss on human teeth. More particularly, the present invention relates to flossers that contain a strand of floss. Additionally, the present invention relates to flosser apparatus which have the ability to tighten the floss.

BACKGROUND OF THE INVENTION

It has been well known in the past to provide some form of an implement to facilitate the removing of food particles from between a person's teeth. Such items have been frequently referred to as a toothpick and generally take the form of an elongated pointed tool which is adapted to be inserted between a person's teeth and moved in order to dislodge any food particles and plaque located between the teeth.

It has been further found to be desirable to not only employ the use of a pointed instrument, but also to employ the use or a strand of thread which is commonly referred to as dental floss. A segment from the dental floss is to be stretched taut and then inserted between the person's teeth and moved back and forth in order to effect removal of any lodged food particles and plaque.

Over time, various persons have discovered that it is practical and useful to apply a segment of a strand of dental floss into an implement that can be inserted into the mouth and manipulated so as to properly control the application of the floss. These devices are commonly known as "flossers". These devices provide a convenient mechanism for the flossing of teeth without the need for lengthy strands of floss. They also serve to more effectively reach into the spaces between the teeth so as to carry out flossing activities in a more effective manner.

In the past, various patents have issued relating to such flosser implements.

The earliest flosser apparatus that was revealed is in U.S. Pat. No. 2,187,899, issued on Jan. 23, 1940 to I. Henny. This patent describes a dental floss throw-away unit in which a single strand of thread extends between outwardly extending arms. A head is formed with the arms extending radially outwardly therefrom. The strand of floss extends in parallel relationship to the back of the head.

U.S. Pat. No. 2,648,341, issued on Aug. 11, 1953 to S. Moll teaches a dental floss holder which includes an elongated flexible member formed of plastic material. One end of the flexible member is rounded and provided with a transverse bore. A length of dental floss will extend through the transverse bore.

German Patent No. 29 23 057 teaches a dental floss applicator which includes a plurality of strands of floss which are far apart and extend in a plane which is perpendicular to the holder portion. Since the strands are not aligned with the shank portion of this flosser device, they are relatively difficult to apply as floss to one's teeth. The flosser is removably secured within a U-shaped head portion.

U.S. Pat. No. 4,280,518, issued on Jul. 28, 1981 to S. M. Gambaro teaches a tooth cleaning implement which includes an elongated member which has, at one end, a strand of dental floss tautly stretched thereacross. The opposite end of the elongated member is attached to a brush-like member which is used to facilitate the cleaning of teeth and dental bridges.

U.S. Design Pat. No. 276,088, issued on Oct. 23, 1984 to A. Fong describes a conventional flosser apparatus in which a single strand of floss is retained between a pair of arms extending outwardly of a head portion. A strand is connected to the head portion and extends so as to terminate at a pointed end.

U.S. Pat. No. 4,522,216, issued on Jun. 11, 1985, to R. L. Bunker describes a dental floss applicator which comprises a solid rectangular shaped body fitted with a pair of adjacent end arms forming a yolk arrangement in which the floss is drawn so as to form an X-shaped pattern. A small button fastener on each side of the applicator body permits the fastening of the floss after it has been stretched taut around the yolk.

German Patent No. 3,831,039 issued to H. Bauer describes a device for cleaning the narrow space between a bridge and the jaw. A pair of threads are connected to a guide. The threads are arranged in parallel to each other and are connected to each other by a number of parallel transverse threads.

U.S. Pat. No. 5,016,660, issued on May 21, 1991 to M. S. Boggs describes an automatic flossing tool having reciprocating tines supporting the flossing material and biased apart so as to assure proper tension on the flossing material. The device includes a means carried out by the tines for moving the flossing material between the tines and having a removable head so as to permit replacement of the head to provide sterile use for subsequent users.

In the recent past, it has been recognized that the above-identified flosser designs are often faulty because of the difficulty in placing the floss between the teeth and the difficulty associated with removing the floss from the teeth. In other circumstances, the close spacing of teeth will make it difficult to place the floss, in a slackened condition, between the teeth. Since the floss between the arms of the flosser apparatus of these prior designs is not in a very "tensioned" condition, then the floss can become frayed when placed in between and pulled out of the teeth. In order to overcome this problem, various U.S. patents have recently issued relating to the flosser apparatus with the ability to "tension" the strand prior to application and removal from the teeth. U.S. Pat. No. 5,538,023, issued on Jul. 23, 1996 to Oczkowski et al., describes a tensioning dental flosser having a holder, a bow and a length of dental floss spanning the bow. A movable element is provided which can cause a portion of the floss holder to move and tighten the strand of floss so as to reduce the slack in the floss. U.S. Pat. No. 5,692,531, issued on Dec. 2, 1997 to I. S. Chodorow, describes a dual strand dental flosser having a body part, first and second spaced apart arms extending from the body part, a first strand of dental floss extending axially between the arms and a second strand of dental floss extending axially between the arms and generally parallel to the first strand of dental floss. A lever mechanism extends from one of the arms which is movable so as to be moved toward the body part. When this lever is moved toward the body part, the first and second strands will tighten. U.S. Pat. No. 5,829,458, issued on Nov. 3, 1998 to I. S. Chodorow, describes a dental floss holder of similar construction to that of U.S. Pat. No. 5,692,531. It shows a variety of other mechanisms that can be used for tightening the dental floss.

There is a product on the market identified as the "GLIDE (TM)" floss pick and manufactured by W. L. Gore and Associates, Inc. This is another type of flosser that includes a tensioning structure. In this device, the handles of the flosser can be squeezed together so as to cause the floss-holding arms to move away from each other about a pivot point spaced from the floss and between the floss and the pivot point.

Unfortunately, in all of these prior art devices, the technique for tensioning the floss will require the application of pressure generally in the direction of the floss. However, when the floss is applied to the teeth, a force must be applied transverse to the floss so as to cause the floss to enter the spaces between the teeth. In each of these prior art devices, by applying forces in the direction of the floss, there is a difficulty in manipulating the head of the flosser so that the floss will enter the spaces between the teeth. Often, the tension-providing surfaces will be somewhat wet so as to create a sliding motion of the fingers placed thereon. It is very difficult to manipulate the flosser so that the tensioned floss is manipulated in the desired manner. Also, subsequent to use, it is difficult to tension the floss and then carry out a lifting motion whereby the floss can be removed from the teeth.

It is an object of the present invention to provide a flosser apparatus which facilitates the tensioning and relaxing of tension from the floss at the end of the flosser.

It is another object of the present invention to provide a flosser apparatus which causes the tension-providing force to be applied in a direction transverse to the direction of the floss.

It is another object of the present invention to provide a flosser apparatus whereby the floss can be more easily manipulated during the flossing of teeth.

It is a further object of the present invention to provide a flosser apparatus which avoids the shredding of the floss during use.

It is still another object of the present invention to provide a flosser apparatus which is easy to use, relatively inexpensive and easy to manufacture.

These and other objects and advantages of the present invention will become apparent from a reading of the attached specification and appended claims.

BRIEF SUMMARY OF THE INVENTION

The present invention is a flosser apparatus having a body with a first fork member and a second fork member at an end thereof, a flexible member interposed between the fork members, and a length of floss having one end affixed to the first fork member and an opposite end affixed to the second fork member. The length of floss extends in a direction. The flexible member is cooperative with the fork members such that the first and second fork members move away from each other upon the application of a force onto the flexible member in a direction transverse to the direction of the length of the floss.

In the present invention, the body has a pivot point between the first and second fork members on a side of the flexible member opposite the length of floss.

In the preferred embodiment of the present invention, the flexible member is a tubular member having one side affixed to the first fork member and an opposite side affixed to the second fork member. This tubular member has a longitudinal axis extending transverse to the direction of the length of floss.

In another embodiment of the present invention, the flexible member comprises an arcuate member having one end affixed to the first fork member and an opposite end affixed to the second fork member. Each of the first and second fork members can either have a bent shape such that the length of floss is offset from the plane of the body or can be of a planar shape. The body has a pointed end at an end opposite the length of floss.

DETAILED DESCRIPTION OF THE INVENTION

Figure 1:
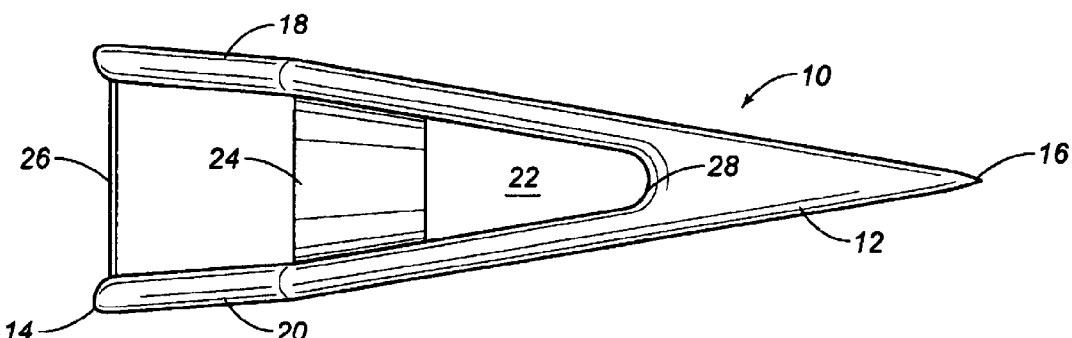
FIG. 1 is a plan view of the preferred embodiment of the present invention.

Referring to FIG. 1, there is shown at 10 the flosser apparatus in accordance with the preferred embodiment of the present invention. The flosser apparatus 10 includes a body 12 having a fork end 14 and a pointed end 16. The fork end 14 includes first fork member 18 and second fork member 20. A space 22 is defined between the fork members 18 and 20. A flexible member 24 is interposed between the first fork member 18 and the second fork member 20 in the space 22. A length of floss 26 has one end affixed to the first fork member 18 and an opposite end affixed to the second fork member 20. The length of floss 26 extends in a particular direction. In the present invention, the flexible member 24 is cooperative with the first fork member 18 and the second fork member 20 such that the fork members 18 and 20 move away from each other upon an application of force onto the flexible member 24 in a direction transverse to that of the direction of the length of floss 26.

In FIG. 1, it can be seen that the body 12 has a pivot point 28 positioned on a side of the flexible member 24 opposite the length of floss 26. The fork members 18 and 20 will pivot with respect to the pivot point 28 on the body 12. The opposite end 16 has a pointed configuration. The body 12 has a generally chevron configuration. The pointed end 16 serves as a pick in the nature of a toothpick. The body 12 is formed of a polymeric material through an injection molding process. The floss 26 can be a single strand of floss or multiple floss strands arranged in parallel. The floss 26 can be of various materials similar to those used in existing flossers.

Figure 2:
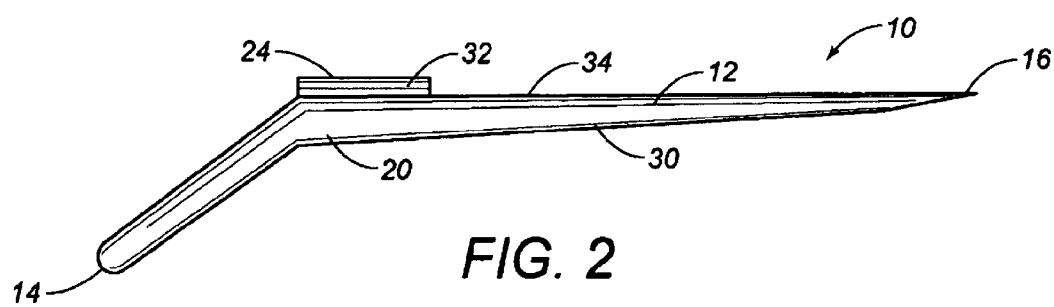
FIG. 2 is a side elevational view of the preferred embodiment of the present invention.

In FIG. 2, it can be seen that the body 12 of the flosser apparatus 10 has a planar portion 30 extending from the end 16 to the end of the flexible member 24. It can be seen that the flexible member 24 has a surface 32 which extends above the top surface 34 of the body 12. The second fork member 20, as illustrated in FIG. 2, is bent downwardly so that the floss will extend in an offset plane from that of the body 12.

Figure 3:
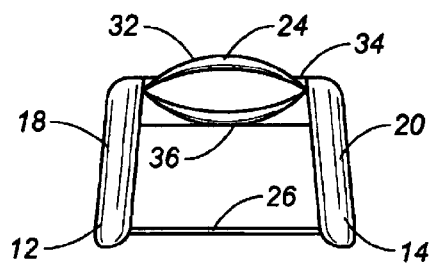
FIG. 3 is an end view of the preferred embodiment of the present invention.

FIG. 3 shows an end view of the end 14 having fork members 18 and 20 supporting the length of floss 26 therebetween. The flexible member 24 is illustrated as having its sides affixed, respectively, to the fork members 18 and 20.

Importantly, in FIG. 3, it can be seen that the flexible member 24 has a generally tubular configuration. This tubular configuration has a top surface 32 extending above the top surface 34 of the flosser body 12. In normal use, the length of floss 26 will be in a relatively slackened condition when no pressure is applied to the tubular member 24. However, when the top surface 32 and the bottom surface 36 of the tubular member 24 are pressed together, this will cause a corresponding expansion of the fork members 18 and 20 away from each other. The application of forces upon surfaces 32 and 36 will be in a direction transverse to the direction of the length of floss 26. When compressed, the floss 26 is in a tightened condition so that it can easily be inserted between the teeth. During actual flossing, the flexible member 24 can be released so that the surfaces 32 and 36 return to their original position. Subsequent to flossing, the surfaces 32 and 36 can be compressed together so as to tighten the length of floss 26 to allow for easy removal of the floss 26 from between the teeth.

The application of forces upon surface 32 facilitates the insertion of the length of floss 26 between the teeth. Since a downward force is applied to surface 32 of flexible member 24, the same downward force will be imparted to the fork members 18 and 20 and to the floss 26 extending therebetween. When a force is applied to surface 36, there is an upward force which will facilitate the "lifting" of the floss 26 from the area between the teeth. In all circumstances, this transverse application of force, relative to the floss 26, facilitates the proper manipulation of the flosser apparatus 10 of the present invention during flossing activities. The grasping of the surfaces 32 and 36 allows the application of strong pinching forces when they are needed most, i.e. during the application and removal of the floss from the teeth.

Figure 4:
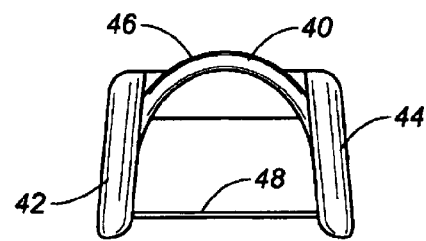
FIG. 4 is an end view of an alternative embodiment of the present invention.

FIG. 4 shows an alternative embodiment of the present invention in which a single arcuate member 40 is interposed between fork members 42 and 44. In the configuration of FIG. 4, a downward compressive force upon the top surface 46 of the arcuate member 40 will cause the fork members 42 and 44 to spread away from each other so that the floss 48, extending therebetween, will be in a tensioned condition. In the embodiment of FIG. 4, the flexible member 40 is not a "tubular member" but simply half of a tubular member or an arcuate portion. The simple embodiment of FIG. 4 facilitates the application of the floss 48 into the space between the teeth but does not inherently facilitate the removal of such floss 48 from between the teeth.

Figure 5:
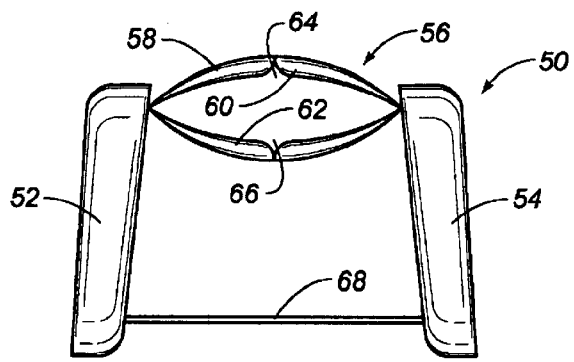
FIG. 5 shows a second alternative embodiment of the present invention in an uncompressed condition.

FIG. 5 shows another alternative embodiment 50 of the flosser apparatus of the present invention. Embodiment 50 includes a body similar to that of the previous embodiment, along with fork members 52 and 54. The flexible member 56 is made up of a tubular member 48 having a top portion 60 and a bottom portion 62. The top portion 60 has its ends secured to the fork members 52 and 54, respectively. The bottom portion 62 has its ends also secured to the fork members 52 and 54 in a location common to the ends of the top portion 60. The top portion 60 includes a split 64 therein. Similarly, the bottom portion 62 includes a split 66 therein. The splits 64 and 66 extend longitudinally along the flexible member 56 and facilitate the easy tensioning of the strand of floss 68 between the fork members 52 and 54.

Figure 6:
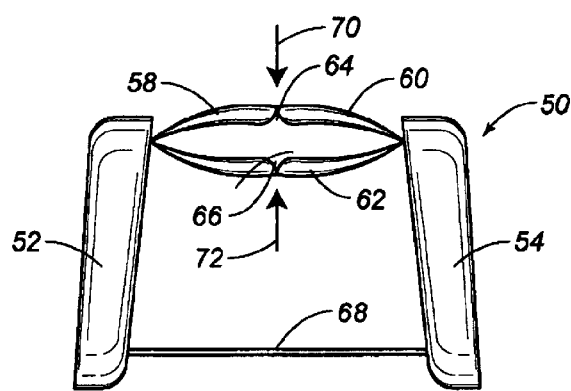
FIG. 6 shows the embodiment of FIG. 5 in a compressed condition in which the floss is tensioned.

In FIG. 5, it can be seen that the strand 68 is in an untensioned condition. The flexible member 56 has no pressure applied thereto. In FIG. 6, it can be seen that a downward pressure 70 is applied to the top portion 60 and an upward force 72 is applied to the bottom portion 62. This causes the fork members 52 and 54 to move away from each other slightly so that the length of floss 68 is suitably tensioned. The respective splits 64 and 66 of the top portion 60 and the bottom portion 62 will spread further apart so as to facilitate the easy compression by the application of forces 70 and 72.

Figure 7:
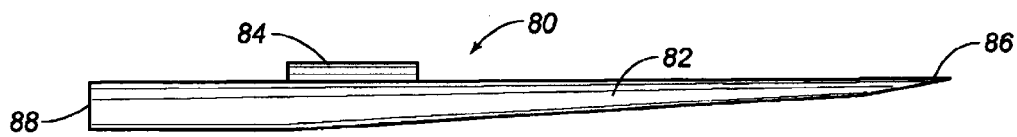
FIG. 7 is a side elevational view of a third embodiment of the present invention.

FIG. 7 shows another alternative embodiment 80 of the present invention. In the alternative embodiment of the flosser apparatus 80, the body 82 has a generally planar configuration. Flexible member 84 is positioned along the length of the body 82 between the ends 86 and 88.

Figure 8:
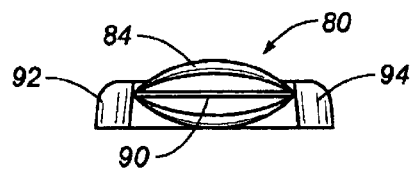
FIG. 8 is an end view of the third embodiment of the present invention.

FIG. 8 shows the end view of the alternative embodiment 80 in which a strand of floss 90 has its ends affixed, respectively, to fork members 92 and 94. Flexible member 84 is illustrated as a tubular member fitted in the space between the fork members 92 and 94.

Figure 9:
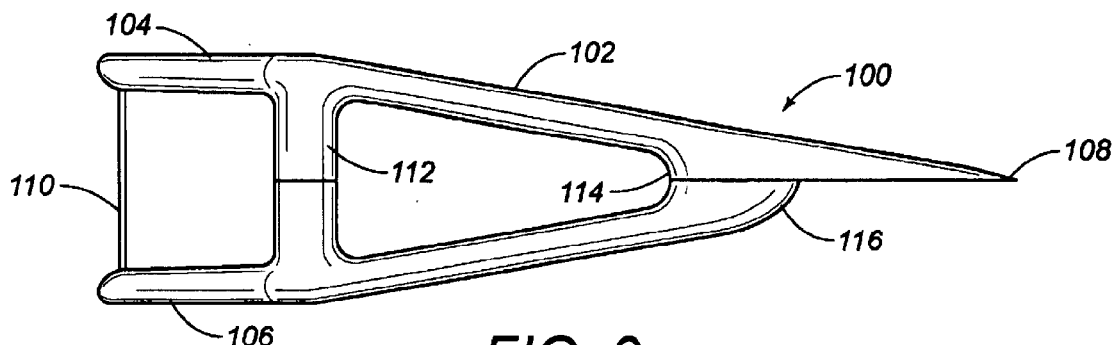
FIG. 9 is a plan view showing a fourth alternative embodiment of the present invention.

FIG. 9 shows another alternative embodiment 100 of the flosser of the present invention. Flosser 100 has a body 102 with fork members 104 and 106 at an end opposite the pointed end 108. A strand of floss 110 will extend between the fork members 104 and 106. Flexible member 112 is positioned between the pivot point 114 of the fork members 104 and 106 and the strand of floss 110. Flexible member 112 is integrally formed with the fork members 104 and 106. It can be seen that fork member 106 has an end 116 which terminates prior to the pointed end 108.

Figure 10A:
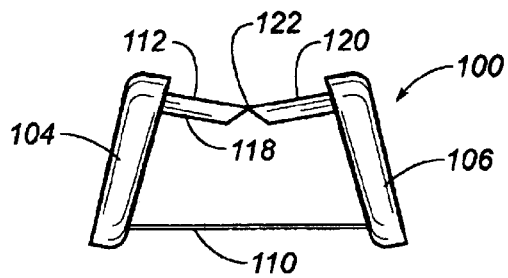
FIGS. 10A–B show the operation of the fourth alternative embodiment of FIG. 9.
Figure 10B:
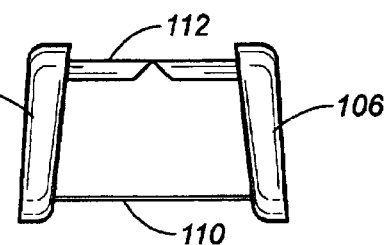

FIGS. 10A and 10B show the operation of the alternative embodiment of the flosser 100. In FIG. 10A, the tensioned condition of the strand 110 is particularly illustrated. As can be seen, the flexible member 112 is formed of a pair of planar members 118 and 120 separated by an inverted V-shaped slot 122. When a pressure is applied to the top surface of the flexible member 112, the fork members 104 and 106 will separate from each other so as to tension the floss 110. When the pressure is released from the flexible member 112, as illustrated in FIG. 10B, the fork members 104 and 106 will move closer to each other thereby the releasing of the tension in the strand of floss 110. As a result, the planar portions 118 and 120 of flexible member 112 will reassume a planar condition extending between the fork members 104 and 106.

Figure 11:
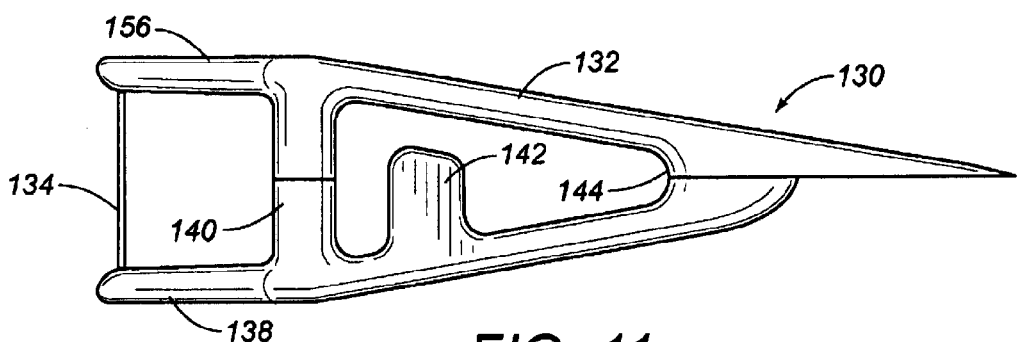
FIG. 11 is a plan view of a fifth alternative embodiment of the present invention.

FIG. 11 shows a fifth alternative embodiment 130 of the flosser of the present invention. Flosser 130 has body 132 having a strand of floss 134 at one end thereof extending between fork members 136 and 138. A flexible member 140 extends between the fork members 136 and 138. Generally, FIG. 11 has a similar configuration to that of FIG. 9. However, a flap 142 extends inwardly from fork member 138 between fork member 138 and fork member 136. The flap 142 terminates before contact with the fork member 136. Flap member 142 is positioned between the pivot point 144 of fork members 136 and 138 and the flexible member 140.

Figure 12A:
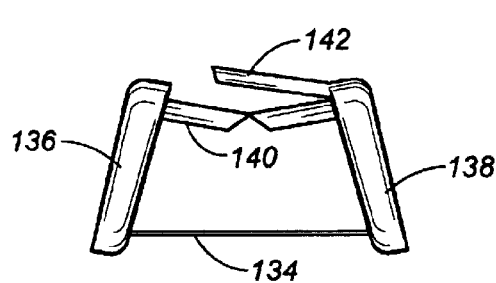
FIGS. 12A–B show the operation of the fifth alternative embodiment of FIG. 4.
Figure 12B:
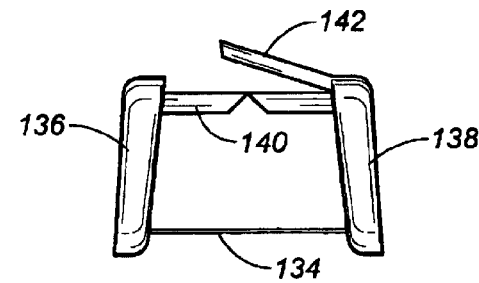

FIG. 12A shows that the flap 142 can be pushed downwardly so as to cause the planar portions of flexible member 140 to become separated thereby pushing the fork members 136 and 138 outwardly so as to tension floss 134. FIG. 12B shows that the pressure on the flap 142 has been released so that the flexible member 140 returns to its planar configuration and the fork members 136 and 138 resume a closer relationship so that the floss 134 is suitably slackened.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A flosser apparatus comprising:
   a body having a first fork member and a second fork member at an end thereof, said first and second fork members having a space therebetween;
   a flexible member interposed between said first and second fork members in said space; and
   a length of floss having one end affixed to said first fork member and an opposite end affixed to said second fork member, said length of floss extending in a direction, said flexible member being cooperative with said first and second fork members such that said first and second fork members move away from each other upon an application of a force onto said flexible member in a direction transverse to said direction of said length of floss, said flexible member comprising a tubular member having one side affixed to said first fork member and an opposite side affixed to said second fork member.

2. The apparatus of claim 1, said tubular member having a longitudinal axis extending transverse to said direction of said length of floss.

3. A flosser apparatus comprising:
   a body having a first fork member and a second fork member at an end thereof, said first and second fork members having a space therebetween;
   a flexible member interposed between said first and second fork members in said space; and
   a length of floss having one end affixed to said first fork member and an opposite end affixed to said second fork member, said length of floss extending in a direction, said flexible member being cooperative with said first and second fork members such that said first and second fork members move away from each other upon an application of a force onto said flexible member in a direction transverse to said direction of said length of floss, said flexible member being of an oval shape having a top portion and a bottom portion, said top portion and said bottom portion having ends affixed respectively to said first and second fork members.

4. The apparatus of claim 3, said top portion having a split formed between the ends thereof, said bottom portion having a split formed between the ends thereof.

5. A flosser apparatus comprising:
   a body having a first fork member and a second fork member at an end thereof, said first and second fork members having a space therebetween;
   a flexible member interposed between said first and second fork members in said space; and
   a length of floss having one end affixed to said first fork member and an opposite end affixed to said second fork member, said length of floss extending in a direction, said flexible member being cooperative with said first and second fork members such that said first and second fork members move away from each other upon an application of a force onto said flexible member in a direction transverse to said direction of said length of floss, said flexible member being of a planar configuration with a split formed between said first fork member and said second fork member.

6. The apparatus of claim 5, of said first fork member and second fork member having a flap extending inwardly toward the other of the fork members, said flap positioned on a side of said flexible member opposite said length of floss.

7. A flosser apparatus comprising:
   a body having a first fork member and a second fork member at an end thereof, said first and second fork members having a space therebetween, said body having a pivot point for said first and second fork members;
   a flexible member interposed between said first and second fork members in said space; and
   a length of floss having one end affixed to said first fork member and an opposite end affixed to said second fork member, said flexible member positioned between said pivot point and said length of floss, said length of floss extending in a direction, said flexible member being cooperative with said first and second fork members such that said first and second fork members move away from each other upon an application of a force onto said flexible member in a direction transverse to said direction of said length of floss.

8. The apparatus of claim 7, said flexible member comprising a tubular member having one side affixed to said first flexible member and an opposite side affixed to said second flexible member.

9. The apparatus of claim 8, said tubular member having a longitudinal axis extending transverse to said direction of said length of floss.

10. A flosser apparatus comprising:
    a body having a first fork member and a second fork member at an end thereof, said first and second fork members having a space therebetween, said body having a pivot point for said first and second fork members, said body being a planar member;
    a flexible member interposed between said first and second fork members in said space; and
    a length of floss having one end affixed to said first fork member and an opposite end affixed to said second fork member, said flexible member positioned between said pivot point and said length of floss.

11. A flosser apparatus comprising:
    a body having a first fork member and a second fork member at an end thereof, said first and second fork members having a space therebetween;
    a tubular member interposed between said first and second fork members in said space; and
    a length of floss having one end affixed to said first fork member and an opposite end affixed to said second fork member, said tubular member being compressible such that a compression of said tubular member causes said length of floss to tighten and a release of compression from said tubular member causes said length of floss to slacken.

12. The apparatus of claim 11, said tubular member having a longitudinal axis transverse to said length of floss and generally in parallel relationship to said body.

* * * * *